United States Patent

Verderber

[11] Patent Number: 5,139,421
[45] Date of Patent: Aug. 18, 1992

[54] MIRROR LIGHT

[76] Inventor: Gregory R. Verderber, 3713 Homewood Rd., Cincinnati, Ohio 45227

[21] Appl. No.: 390,963

[22] Filed: Aug. 8, 1989

Related U.S. Application Data

[63] Continuation-in-part of Ser. No. 92,578, Sep. 3, 1987, abandoned.

[51] Int. Cl.$^5$ .......................... A61B 1/24; A61C 1/00; A61C 3/00
[52] U.S. Cl. .......................................... 433/31; 433/30
[58] Field of Search ...................... 433/30, 31; 128/11, 128/22; 350/640

[56] References Cited

U.S. PATENT DOCUMENTS

| | | | |
|---|---|---|---|
| 1,281,136 | 10/1918 | Clement | 128/11 |
| 1,747,009 | 2/1930 | Jordan | 128/11 |
| 2,088,735 | 8/1937 | Everhards | 128/22 |
| 2,195,526 | 4/1940 | Traver | 350/640 |
| 2,393,319 | 1/1946 | Freedman | 433/29 |
| 2,428,975 | 10/1947 | Lamb | 350/640 |
| 3,032,879 | 5/1962 | Lafitte | 433/30 |
| 3,566,474 | 3/1971 | Zuhlke et al. | 433/30 |
| 3,638,013 | 1/1972 | Keller | 433/31 |

FOREIGN PATENT DOCUMENTS 1932912 1/1971 Fed. Rep. of Germany ........ 433/30

OTHER PUBLICATIONS

"Light Piping with Lexan Resin"-*Lexan Technifacts* Dec. 1982.
Mirolite ® lighted mouth mirror, The Butler Smile Factory, pp. 14 and 15, 1988.

*Primary Examiner*—Gene Mancene
*Assistant Examiner*—Cindy A. Cherichetti
*Attorney, Agent, or Firm*—Jerrold J. Litzinger

[57] ABSTRACT

The present invention consists of a mirror to be used in combination with a light source. Light is transmitted from the light source through the body of a light conductive shank to a shank heel and face, from which illumination is provided in front of and behind the mirror head. In this way, for example, the invention can be used in dentistry both for illuminated, indirect vision in the mouth and as an illuminated cheek or tongue retractor.

The invention can be used in combination with any suitable light source including, but not limited to, a portable pen light type light source (which is maneuverable and easily transportable) or a conventional fiber optic lighting system.

13 Claims, 2 Drawing Sheets

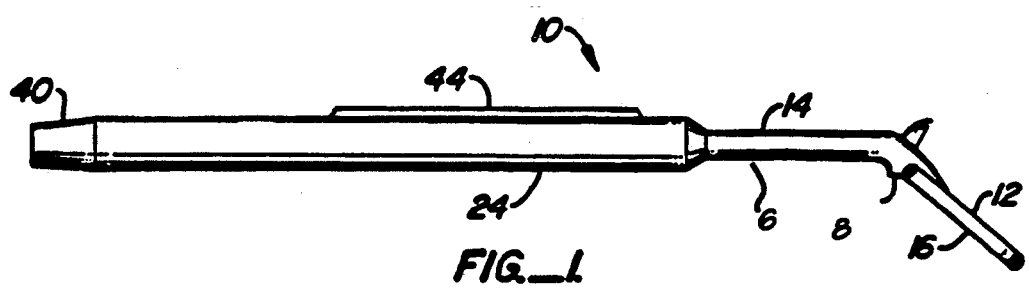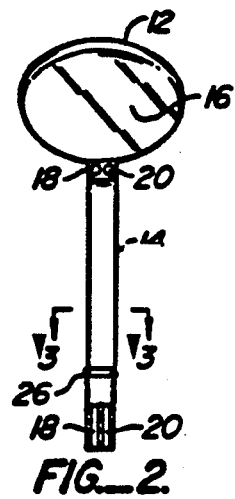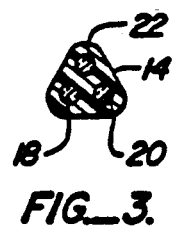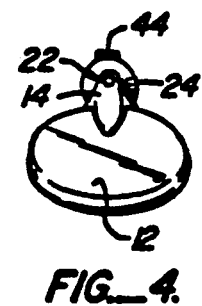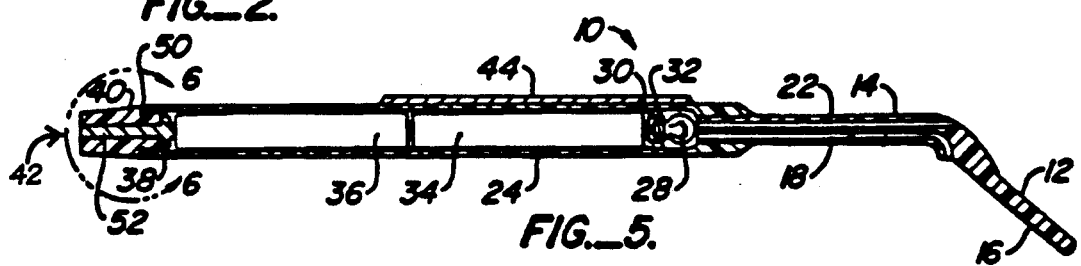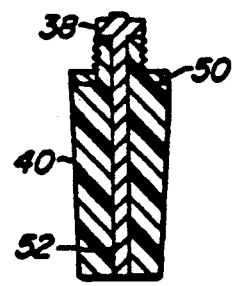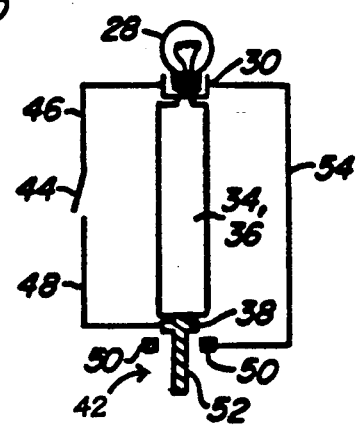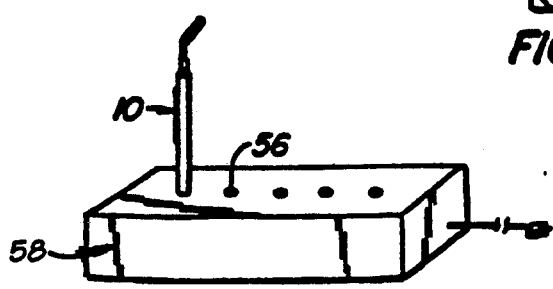

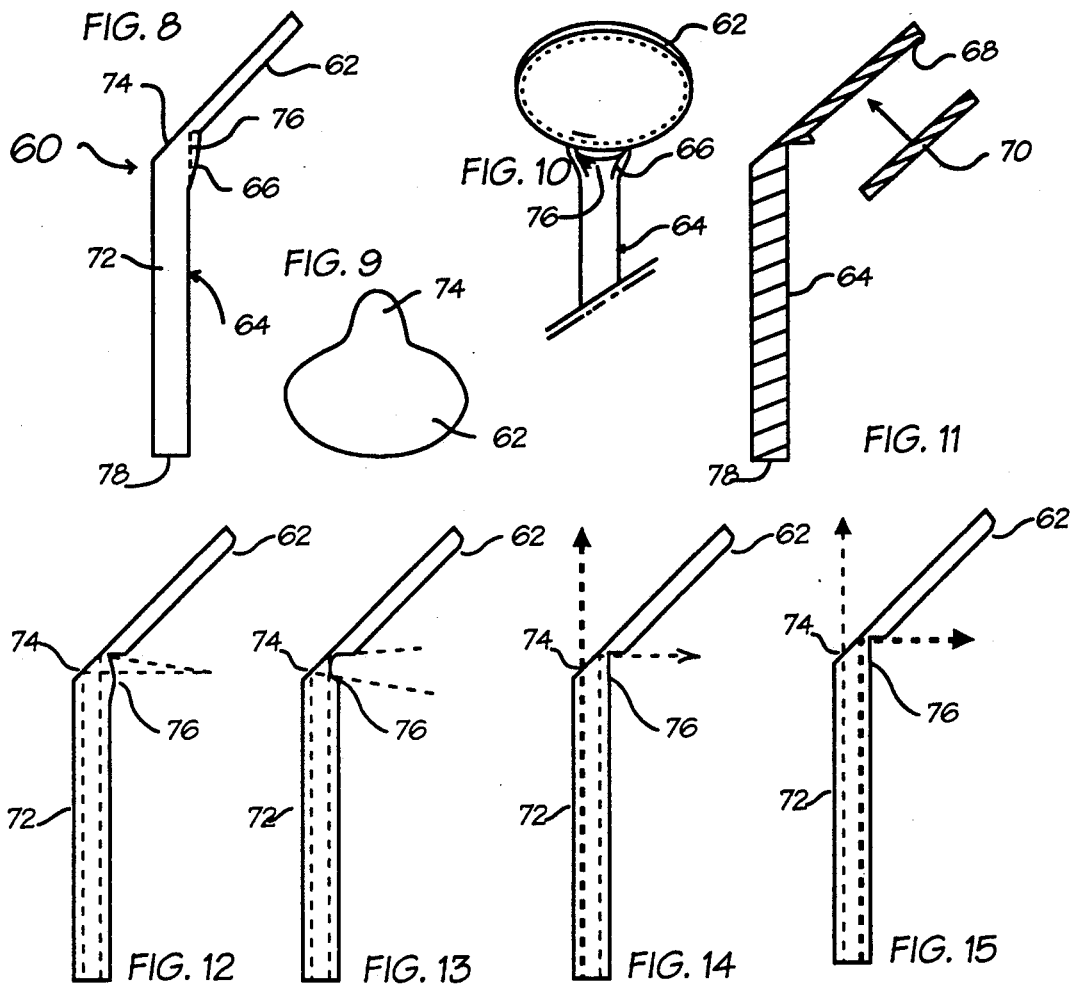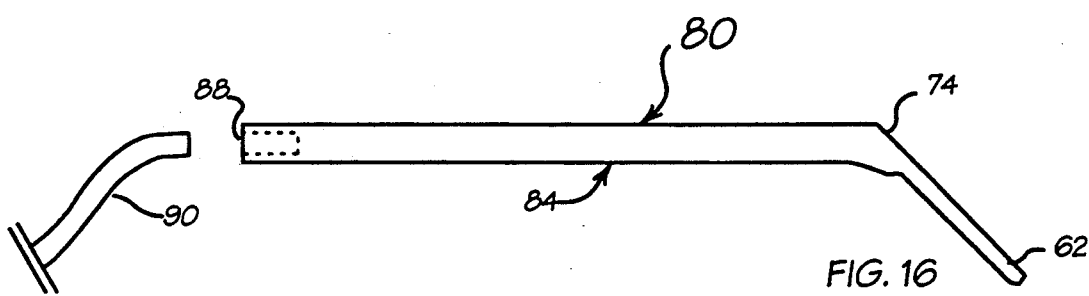

MIRROR LIGHT

This application is a continuation-in-part of Ser. No. 07/092,578, filed Sep. 3, 1987 now abandoned..

BACKGROUND OF THE INVENTION

1. Field of the Invention.

The present invention relates to mirrors used for inspection and examination. More specifically, the invention relates to a dental mouth mirror to be used in combination with a light source.

2. Description of the Prior Art

In dentistry, it has been the practice to use a dental lamp in combination with a dental mouth mirror to assist viewing while performing work in the oral cavity. The dental lamp is a light source providing a large beam of light which may be focused in the general area of a patient's mouth. Thereafter, a dental mirror is used to indirectly view inaccessible areas of the mouth, or to retract the tongue or cheek in order to view an area directly. Such technique has not been entirely satisfactory. A dentist's hands and/or instruments often shade the area which is being viewed, thereby requiring the dentist to assume an awkward position so as not to shade the area being viewed. During an oral examination or dental cleaning, where each tooth and various other structures are observed and manipulated, the dental lamp must constantly be adjusted, resulting in considerable time loss and frustration.

More recently, dental instruments, including the dental mirror, have been combined with fiber optics. U.S Pat. No. 3,638,013, to Ronald F. Keller, discloses a fiber optic lighting system providing a fiber optic cable which transmits light from a distant light source to illuminate the area of the mouth in which an instrument is being used. Further, the combination of a fiber optic cable and an air driven dental drill is well known and has been well accepted In such combination, the fiber optic cable is incorporated into the tubing which supplies air power to the dental drill.

Unfortunately, prior art combinations of a fiber optic cable with a dental mouth mirror, like that of the Keller reference, have proven to be unacceptable. Such combinations have been cumbersome and significantly limited the maneuverability of the mouth mirror. Moreover, such combinations are not readily transportable and can only be used in suitably equipped dental operatory.

Further, the Keller dental mouth mirror has provided for light to be emitted from the viewing surface of the mirror. Such an embodiment directs light through the mirror, which requires custom mirrors where reflective material has been removed. Such mirrors are technically difficult and prohibitively expensive to manufacture. Accordingly, it would be desirable to provide an illuminated dental mirror using conventional glass or acrylic mirrors which are available at low cost.

Still further, when a portion of the reflective material on the mirror is removed so that light can pass through and be emitted from the surface of the mirror, the usable viewing area of the mirror is significantly reduced. The viewing area is also interrupted by the presence of a halo about the mirror surface where light is emitted. When performing intricate tasks, as is common in dentistry, the mirror must be held in such a way as to avoid these areas. It is frustrating for the dentist and may be dangerous for the patient to have such areas block or distort the field of view during critical procedures.

Additionally, existing combinations of a light source with a dental mouth mirror do not provide for light to be projected behind the reflective surface of the mirror. This is very useful when the mirror is used as a tongue or cheek retractor, which is common in dentistry.

In general, it is an object of the present invention to provide a dental mouth mirror which illuminates oral structures during dental or medical procedures.

Another object of the invention is to provide a dental apparatus of the above character where objects can be easily viewed in the mirror.

Yet another object of the invention is to provide a dental apparatus of the above character which can be readily and economically manufactured.

Another object of the invention is to provide a dental apparatus of the above character where the portion used in the oral cavity may be disposed of after a single use so as to prevent cross contamination and reduce the risk of infection in the dental or hospital environment.

Another object of the invention is to provide a dental apparatus of the above character which is light and compact.

SUMMARY OF THE INVENTION

The present invention consists of a mirror to be used in combination with a light source. Light is transmitted from the light source through the body of a light conductive shank to a shank heel and face, from which illumination is provided in front of and behind the mirror head. In this way, for example, the invention can be used in dentistry both for illuminated, indirect vision in the mouth and as an illuminated cheek or tongue retractor.

The invention can be used in combination with any suitable light source including, but not limited to, a portable pen light type light source (which is maneuverable and easily transportable) or a conventional fiber optic lighting system.

BRIEF DESCRIPTION OF THE DRAWING

While the specification concludes with claims particularly pointing out and distinctly claiming the present invention, it is believed the same will be better understood from the following description taken in conjunction with the accompanying drawing in which:

FIG. 1 is an elevational view of the mirror light made in accordance with the present invention.

FIG. 2 is a partial view of the mirror light shown in FIG. 1 specifically depicting the mirror head and shank.

FIG. 3 is a cross-sectional view taken along section line 3—3 of FIG. 3 showing the inside of the shank.

FIG. 4 is a side elevational view of the mirror light in FIG. 1.

FIG. 5 is a cross-sectional view of the mirror light in FIG. 1.

FIG. 5A is a schematic drawing of the electrical components of the mirror light depicted in FIG. 1.

FIG. 6 is an enlarged cross-sectional view of a recharge adapter to be utilized with the mirror light of FIG. 1.

FIG. 7 is a perspective view of the mirror light shown in FIG. 1 inserted into the receptacle of a battery recharger.

FIG. 8 is a partial side view of a second embodiment of the mirror light specifically depicting the mirror head and shank.

FIG. 9 is a top view of the mirror light in FIG. 8.

FIG. 10 is a partial front view of the mirror light in FIG. 8.

FIG. 11 is a partial sectional view of the mirror light in FIG. 8 indicating placement of a conventional round glass or acrylic mirror in the mirror head.

FIG. 12 is a view of the mirror light in FIG. 8 showing the optical effect of a convex face.

FIG. 13 is a view of the mirror light in FIG. 8 showing the optical effect of a concave face.

FIG. 14 is a view of the mirror light in FIG. 8 showing the optical effect of increasing the angle of the heel relative to the shank.

FIG. 15 is a view of the mirror light in FIG. 8 showing the optical effect of decreasing the angle of the heel relative to the shank.

FIG. 16 is an elevational side view of the mirror light depicted in FIG. 8 with extended shank and fiber optic cable adapter.

DESCRIPTION OF THE PREFERRED EMBODIMENTS

For the purpose of promoting an understanding of the principles of the present invention, reference will now be made to the embodiments illustrated in the drawing (where like numerals indicate like elements of the invention) and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The invention is described and specific references are made relating the invention to the art of dentistry; however, such descriptions and embodiments in no way limit the use of the present invention to the dental field. The mirror light of the present invention has practical applications in many fields including, but not limited to, medicine, industry, hobby and automotive.

A mirror light 10 is shown in FIGS. 1, 4, 5, and 7 consisting of a pen light type light source and a dental mouth mirror. Mirror light 10 comprises three major segments, including a handle 24, a shank 14 and a head 12. Shank 14 further includes a body 6, a heel 7, and a face 8.

Head 12 and depending shank 14 are formed of molded plastic or other suitable material. Head 12 is inclined at a predetermined angle to shank 14, which preferably is approximately 45 degrees. A mirror surface 16 of coated glass or other suitable reflective material is inset or molded into mirror head 12. Within shank 14 are contained three fiber optic light pipes 18, 20, and 22, which are capable of transmitting light and are well known to those skilled in the art. Light pipes, 18, 20, and 22 may be of any suitable diameter, but by way of example, light pipes with a diameter of 2 millimeters are acceptable for this application. Each of light pipes 18, 20, and 22 within shank 14 is positioned parallel to the longitudinal axis of shank 14. Referring now to FIG. 5, as the light pipes 18, 20, and 22 approach mirror head 12, light pipe 18 and light pipe 20 (not shown) arc approximately 90° and terminate at the edge of face 8 so that the cones of light emitted from them will illuminate structures observed in front of mirror surface 16. Third light pipe 22 does not arc, but remains parallel to the longitudinal axis of shank 14 and terminates at the edge of heel 7 as shown in FIGS. 4 and 5. Light emitted from third light pipe 22 will illuminate structures behind mirror head 12, and is especially helpful for objects observed when mirror head 12 is used to retract the tongue or cheek as is common in dentistry.

Handle 24 of mirror light 10 is composed of molded plastic or other suitable material, which is formed into a cylinder or tube. The opening at one end of the tube is formed so as to securely accept shank 14. Shank 14 can be removably inserted into handle 24 with the longitudinal axis of shank 14 parallel to the longitudinal axis of handle 24. Alternatively, shank 14 can be bonded or glued in handle 24 so that shank 14 is not separable from handle 24. Shank 14 is formed with a rim 26 (as shown in FIG. 2) so that shank 14 can be inserted only a predetermined distance into handle 24. Because shank 14 and head 12 are separable from handle 24, shank 14 and mirror head 12 can be easily and effectively sterilized, disinfected or replaced. When shank 14 is in place in handle 24, one end of fiber optic light pipes 18, 20 and 22 contained within shank 14 are facing and in close proximity to light source 28 in handle 24.

Within handle 24, a socket 30 of conventional type is mounted in a bracket 32. Bracket 32 is formed so that socket 30 will snap into place in handle 24. A lamp 28 of suitable type (for example, a krypton bulb) is mounted in socket 30.

Handle 24 has an internal diameter and length such that two cylindrical batteries 34 and 36 can be inserted with their positive electrodes facing socket 30 as shown in FIG. 5. When batteries 34 and 36 are in place, the positive electrode of battery 34 will contact socket 30 and the negative electrode of second battery 36 will contact a core and disc unit 42 of a recharge adapter 40.

A switch 44 of conventional type is mounted in handle 24, as shown in FIGS. 1, 4 and 5, so that it is accessible to the operator during use of mirror light 10. As seen in the schematic diagram of FIG. 5A, a wire 46 connects switch 44 to socket 30. A wire 48 is also connected to switch 44 and contacts core and disc unit 42 of adapter 40, with adapter 40 threaded into place in handle 24. When pressure is applied to switch 44, the circuit described above and illustrated in the left hand side of FIG. 5A is completed and lamp 28 will light.

The opening in handle 24 opposite shank 14 is internally threaded so as to accept the threaded male section of recharge adapter 40. Recharge adapter 40 can be manually screw threaded for engagement or disengagement to handle 24. By separating the two sections, it is possible to remove and replace batteries 34 and 36 in handle 24. Recharge adapter 40 is formed of plastic or other suitable material and it has a ring 50 around the base of the threaded male section as shown in FIG. 6.

Ring 50 is composed of metal capable of efficiently conducting electric current. Adapter 40 also has a core 52 and disc 38 which are formed as a single unit 42 and are also composed of a conducting metal. Core 52 passes through the center of adapter 40 and disc 38 forms the end to the threaded male segment of adapter 40.

When adapter 40 is threaded into Place in handle 24, as shown in FIG. 5 and schematically in FIG. 5A, core 52 contacts the negative electrode of battery 36. Ring 50 also contacts wire 54, which is connected to socket 30 as shown in the schematic drawing of FIG. 5A. Socket 30 also contacts the positive electrode of battery 34. Adapter 40 is designed in this way so that mirror light 10 can be inserted into a female receptacle of a battery charger 58 of conventional design (shown in FIG. 7).

Electrodes in a receptacle 56 of charger 58 contact ring 50 and core 52 of adapter 40, completing the circuit described above and illustrated in the right hand side of FIG. 5A. In this way, batteries 34 and 36 can be charged while mirror light 10 is not in use.

A second embodiment of the invention is shown in FIGS. 8-16. In this embodiment, a mirror element 60 includes a head 62 and dependent shank 64. However, head 62 and shank 64 are manufactured from a light conductive material such as a plastic acrylic. Head 62 is again generally disc-shaped and is inclined at a predetermined angle 63 to shank 64 material. Structural triangular supports 66 stabilize head 62 where it is attached to shank 64. Within the front surface of mirror head 62, a recess 68 is provided into which a conventional round mirror 70 may be inset or cemented (as shown in FIG. 11).

Shank 64 is generally cylindrical in shape and comprises three major segments, including a body 72, a heel 74 and a face 76. Heel 74 of shank 64 is a planar surface inclined at a predetermined angle 63 to the longitudinal axis of shank body 72. This angle 63 is generally the same angle at which head 62 is inclined in relation to the longitudinal axis of body 72.

Referring now to FIGS. 8 and 10, face 76 is a flattened or planar surface at the junction of mirror head 62 and shank 64, and is generally parallel to the longitudinal axis of the body 72 of the shank 64. The end of shank 64 opposite mirror head 62 is formed so that it may be removably inserted into a female receptacle of a light source, as shown in FIGS. 1 and 5 and more fully described above. The end of shank 64 forms a planar surface 78, which is perpendicular to the longitudinal axis of body 72. When mirror element 60 is used in combination with a light source, planar surface 78 faces, and is in close proximity to, the light source.

Light traveling through shank body 72 from a light source is emitted from heel 74, as well as internally reflected and emitted from face 76. The relative volume of light which is emitted from heel 74, or which is internally reflected and emitted from face 76, is a function of the critical angle for the material used for shank 64 and the included acute angle 63 of heel 74 in relation to the longitudinal axis of body 72. For example, plastic acrylic has a critical angle of 42.2.

Varying the included acute angle of heel 74 in relation to the longitudinal axis of shank 64 will cause more or less light to be directed in front of or behind mirror head 62, depending on the critical angle of the light conductive material utilized. Moreover, by varying the included acute angle of heel 74 in relation to the longitudinal axis of shank 64, more or less light may be provided in front of mirror head 62 and a suitable mirror element 60 can be designed for specific needs. Arrows A and B in FIGS. 14 and 15 show the effect on the volume of light reflected and emitted when the angle between heel 74 and body 72 is varied.

Additionally, face 76 of shank 64 can be formed as a lens so as to focus the light emitted from face 76 (as shown in FIGS. 12 and 13). Forming face 76 of shank 64 as a convex lens will cause light emitted from face 76 to converge as shown in FIG. 12. Forming face 76 as a concave lens will cause light emitted from face 76 to diverge as shown in FIG. 13. Specific lens arrangements can be designed and manufactured in order to allow mirror element 60 to suit very specific needs.

Embodiments of mirror element 60 may be used in connection with a pen light type light source as fully described above and as shown in FIGS. 1 and 5. Additionally, shank 64 of mirror element 60 can be adapted so that mirror element 60 can be used with any suitable light source including, but not limited to, a conventional fiber optic lighting system as described below.

In FIG. 16, mirror element 80 is shown where an extended shank 84 serves as both a handle and transmission means for the mirror element 80. In this embodiment, a female receptacle 88 is provided at one end of shank 84 so that mirror element 80 can be coupled with a conventional fiber optic cable 90. Fiber optic cable 90 is capable of transmitting light from a fiber optic light source (not shown), as is well known to those skilled in the art, so that mirror element 80 works under the same principles of mirror element 60 described above.

What is claimed is:
1. A light emitting instrument, comprising:
   (a) a head having a forward surface and a rear surface, at least one of which is mirrored;
   (b) a shank, comprised of a light conductive material, said shank further comprising:
      (1) a body having a first end and a second end, said first end being connected to said head;
      (2) a heel comprising a planar surface angularly related to the longitudinal axis of said body; and
      (3) a face comprising a planar surface substantially parallel to the longitudinal axis of the body, wherein light applied to said second end of the shank body is transmitted through said shank body to said heel, where at least a portion of the light is reflected to and emitted from the shank face, thereby illuminating the area in front of said head.

2. The light emitting instrument of claim 1, wherein said head and said shank are a one-piece construction.

3. The light emitting instrument of claim 1, wherein the face of said shank is adjacent the forward surface of said head.

4. The light emitting instrument of claim 3 further comprising supports between the face of said shank and said head.

5. The light emitting instrument of claim 1, wherein light to said second end of the shank body is transmitted through said shank body at least a portion of said light is emitted from said shank heel behind the rear surface of said head.

6. A mirror light, comprising:
   (a) a head having a forward surface and a rear surface, at least one of which is mirrored;
   (b) a shank made of light conductive material, said shank further comprising:
      (1) a body having a first end and a second end, said first end being connected to said head;
      (2) a heel comprising a planar surface angularly related to the longitudinal axis of said body; and
      (3) a face comprising a planar surface substantially parallel to the longitudinal axis of said body;
   (c) a handle having an opening wherein the second end of the shank body is receivable therein;
   (d) a light source contained within said handle adjacent said opening, wherein light may be applied to the second end of said shank body;
   (e) means for supplying energy to said light source; and
   (f) means for activating and deactivating said energy to said light source,
wherein light applied to the second end of the shank body by said light source is transmitted through said shank body to said shank heel, at least a portion of the light being internally reflected to the shank face and emitted from the shank face in front of the forward surface of said head.

7. The mirror light of claim 6, wherein at least a portion of light applied to the second end of the shank body by said light source is transmitted through said shank body and is emitted from said shank heel.

8. The mirror light of claim 7, wherein the relative amount of light emitted from said shank heel and the amount of light internally reflected from said shank heel to said shank face is dependent upon the angle of said shank heel to the longitudinal axis of said shank body.

9. The mirror light of claim 7, said shank face being formed as a concave lens, wherein light diverges therefrom.

10. The mirror light of claim 7, said shank face being formed as a convex lens, wherein light is converged toward a particular point.

11. A light emitting instrument, comprising:
 a) a head having a forward surface and a rear surface at least one of which is mirrored; and
 b) a shank, said shank further comprising:
  (1) a body having a first end and a second end said first end being connected to said head;
  (2) a face comprising a planar surface substantially parallel to the longitudinal axis of said body, with said body containing at least one fiber optic light pipe which originates at said second end of said body and terminates behind said rear surface of said head, and said body containing at least one fiber optic light pipe which originates at said second end of said body and terminates at said shank face;
 wherein light applied to said second end of said second end of said shank body is transmitted through a fiber optic light pipe and emitted behind said rear surface of said head, and is transmitted through a fiber optic light pipe and emitted from said shank face in front of said forward surface of said head.

12. The light emitting instrument of claim 11, wherein the face of said shank is adjacent the forward surface of said head.

13. The light emitting instrument of claim 11, further comprising supports between the face of said shank and said head.

* * * * *